United States Patent
Rashidbaigi et al.

[11] Patent Number: 5,989,441
[45] Date of Patent: Nov. 23, 1999

[54] RECOVERY OF FUNCTIONAL HUMAN LEUKOCYTES FROM RECYCLED FILTERS

[75] Inventors: Abbas Rashidbaigi, Morris Plains; Mei-June Liao, Monmouth Junction; Ji Hua, Hopewell, all of N.J.; Maninder Sidhu, New City, N.Y.

[73] Assignee: Interferon Science, Inc., New Brunswick, N.J.

[21] Appl. No.: 08/996,070

[22] Filed: Dec. 22, 1997

[51] Int. Cl.$^6$ .................................................. B01D 24/46
[52] U.S. Cl. .......................... 210/793; 210/798; 210/411; 435/2
[58] Field of Search .................... 210/435, 791, 210/793, 798, 108, 411, 770; 435/2

[56] References Cited

U.S. PATENT DOCUMENTS

| | | | |
|---|---|---|---|
| 4,416,777 | 11/1983 | Kuroda . | |
| 4,833,077 | 5/1989 | Abe et al. | 435/68 |
| 5,833,866 | 11/1998 | Brown | 210/739 |

OTHER PUBLICATIONS

A. Abbas et al, "Introduction to Immunology", *Cellular and Molecular Immunology*, p. 14, W. B. Saunders Company (1991).

R. Longley et al, "Recovery of Functional Human Lymphocytes from Leukotrap Filters", *J. Immunol. Meth.*, 121:33–38 (1989).

J. Coligan, "Preparation of Human Mononuclear Cell Populations and Subpopulations", *Current Protocols in Immunology*, Section I, Units 7.1–7.2, John Wiley & Sons (1994).

I. Menke–Mollars et al, "Leukocyte Depletion, a Comparison of the 'Leukotrap in–line' Filter System with a Sterile Added 4–bag Speacell–R–500–A Filter System", *Bietr Infusionsther*, 30:152–156 91992) (Abstract).

*Primary Examiner*—W. L. Walker
*Assistant Examiner*—Terry K. Cecil
*Attorney, Agent, or Firm*—Howson and Howson

[57] ABSTRACT

A method of recovering functional human leukocytes from blood filters used to deplete leukocyte content from leukocyte-containing blood-cell suspensions is provided. More particularly, this method involves isolating leukocytes from filters which have been used to purify red blood cells or platelets in isolation from leukocytes by back-flushing the used filters with a hemolysis solution, such as cold ammonium chloride, and collecting the functional human leukocytes.

16 Claims, No Drawings

RECOVERY OF FUNCTIONAL HUMAN LEUKOCYTES FROM RECYCLED FILTERS

FIELD OF THE INVENTION

This invention relates to a new method for the isolation of functional human leukocytes from used leukocyte-depleting filters. More particularly, this method involves isolating leukocytes from filters which have been used to purify red blood cells or platelets in isolation from leukocytes by back-flushing the used filters with a hemolysis solution, such as cold ammonium chloride, and collecting the functional human leukocytes.

BACKGROUND OF THE INVENTION

Blood banking centers fractionate blood into various components such as plasma, erythrocytes, plateletes, and leukocytes. Each of these components is then used for a specific application. The blood cell differential in whole blood is described in A. K. Abbas et al, "Introduction to Immunology", *Cellular and Molecular Immunology*, p. 14, Harcourt Brace Jovanovich, Inc. (1991).

Current methods for isolating erythrocytes, platelets and leukocytes from whole blood include using low-speed centrifugation. According to this method, erythrocytes and platelets are separated from leukocytes based on their density. A top layer containing plasma and platelets is removed for the preparation of plasma and platelets and the middle layer containing leukocytes (buffy coats) may be used for induction of cytokines, such as interferons, for isolation of specific cell types for the study of the immune system or for immunotherapy. The bottom layer which contains erythrocyte-rich red cells may be used in transfusions.

This method of isolating red blood cells or platelets from leukocytes by centrifugation is tedious and often does not result in complete separation of the blood cell types. As a result, blood bank centers have begun to use various filtration units to remove leukocytes from the desired red blood cell or platelet preparations. Examples of these filtration units include the Pall RCM® system of Pall Corporation (East Hills, N.Y.), Leukotrap® RC/PL system of Miles Pharmaceuticals, the LeukoNet® system of HemaSure, Inc. and the Sepacell-R/PL™ system of Baxter Healthcare Corporation. These are online filters which collect blood directly from the human vein, rather than indirectly from the centrifugation system. Such online filter units trap and separate leukocytes from erythrocytes and platelets based on cell size exclusion. The smaller erythrocytes easily pass through the filter while the larger leukocytes remained behind trapped in the filter. These filter systems result in a reduction of leukocytes ranging from 82.2% to 99%, depending on the filter system used. [Beitr Infusionsther, 30:152–156 (1992)]

Typically, filters used to prepare red-blood cell or platelet-rich preparations are discarded. However, prior methods have been reported in which leukocytes which remain trapped behind in the filter units have been recovered. For example, one method involves back-flushing five times with 50 mL phosphate buffered saline ("PBS") at 4° C. using a 60 mL syringe [R. Longley et al, *J. Immuno. Methods*, 121:33–38 (1989)]. The "back-flushing" involves flushing the filters in one direction, opposite to the one which is initially used to remove the leukocytes from the desired preparation. The recovered leukocytes at this point in the purification process, still contain a substantial amount of red blood cells. In order to remove the red blood cells, the eluted leukocyte preparations are then further purified by Histopaque gradient centrifugation. A protocol for the isolation of mononuclear cells by Ficoll-Hypaque gradient centrifugation ("histopaque") is described in J. E. Coligan, *Current Protocols in Immunology*, Section I, Units 7.1–7.2, John Wiley & Sons (1994). The mononuclear cells are collected in the interface layer and washed with PBS. Typically, a total of $2.76+/-1.17 \times 10^8$ leukocytes per filter, having a viability of more than 95%, will be isolated by this two-step process. In a 5–10 ml sample, where one would expect $2 \times 10^9$ leukocytes to be present per filter, this represents a 14% recovery of leukocytes. In comparison to some published methods, where a 70% recovery of buffy coats is generally anticipated, this recovery rate is small. Leukocytes isolated in such a manner have been shown to be functional in response to phytohemagglutinin (PHA), conconavalin (CONA), and pokeweed mitogens (PWM).

The elution of leukocytes from filters is also described in Kuroda et al, U.S. Pat. No. 4,416,777. This method also required a multi-step process to facilitate removal of red blood cells from leukocytes using a variety of elution solutions: PBS in combination with polyvinyl-pyriolidone, sodium casein, polyvinyl-alcohol or gelatin.

In view of the importance of purifying fully functional human leukocytes for the manufacture of therapeutic products and other applications, many attempts have been made to retrieve leukocytes from various sources. However, methods used to date continue to have many drawbacks. For example, the methods of Kuroda et al, U.S. Pat. No. 4,416,777 and Longley et al, supra, are both multi-step and, therefore, tedious processes. The published methods produce a relatively low number of leukocytes per filter unit. In addition, known methods require processing of the filters within 24 hours after blood collection; otherwise the viability of the leukocytes is greatly impaired. As a result, improved methods for retrieving leukocytes from recycled blood product preparation filters continue to be needed.

SUMMARY OF THE INVENTION

The present invention solves the problem referred to above by providing a means for isolating functional human leukocytes from recycled blood product preparation unit filters which are normally used by blood banks to prepare leukocyte-poor blood products and which are commonly discarded after use. More specifically, blood filters are back-flushed with ammonium chloride (0.83%) solution in a one step isolation process. Advantageously, the ammonium chloride elutes leukocytes free from red blood cells.

According to this method, functional leukocytes free from erythrocytes and platelets are retrieved from recycled filters using a peristaltic pump to back-flush leukocytes with an ammonium chloride solution. The ammonium chloride performs a three-fold function in a single step: (a) it flushes leukocytes from the filters, (b) it lyses the red blood cells, and (c) it dissolves clumps which form while the blood is standing. Using this method, the recovery from Leukotrap® filters is between 6 and $8 \times 10^8$ leukocytes per filter unit, i.e., a 30–40% recovery of total leukocytes in one unit of whole blood or 50% recovery of published method for purifying leukocytes directly from whole blood. This represents a substantial improvement over methods used to date. In addition, this method makes possible the recovery of ammonium chloride back-flushed leukocytes having a viability of more than 95% while using a generally discarded source.

DETAILED DESCRIPTION OF THE INVENTION

The present method is advantageous in that it permits a one step recovery of erythrocyte-free leukocytes with a greater recovery of functional leukocytes from generally-discarded filter units. An approximately three fold increase in the amount of functional leukocytes retrieved has been demonstrated by the use of ammonium chloride back-flushing of used filters over previously described methods, which use PBS to back-flush erythrocyte-rich leukocytes followed by Histopaque™ separation, in order to retrieve leukocytes from used filters. The leukocytes recovered by the claimed method are functional, i.e., the cells are capable of being activated by virus or mitogen to produce cytokines, such as interferon, or other immunomodulators.

The method of the present invention represents a significant simplification over previous methods for retrieving leukocytes from filters. The method of the invention involves back-flushing about two times with a minimum of 500 mL of ammonium chloride (between 0.7% (w/v) and 0.9% (w/v), where 0.7% (w/v) means 7 mg/ml or 0.7 g per 100 ml) per filter at between 2° C. and 8° C. using a peristaltic pump or any other equivalent pump, followed by centrifugation to obtain pure leukocytes. This step both flushes the leukocytes from the filters and lyses any remaining red blood cells in the filter.

The yield of functional leukocytes observed with the method of the present invention far surpasses that observed in other methods. Recovery from Leukotrap® filters using the described invention is between 6 to $8 \times 10^8$ leukocytes per filter unit. This recovery is about 50% of published methods for purifying leukocytes directly from whole blood. The leukocyte differential of this preparation is also closely similar to the cell types present in whole blood. See, for example, Testa et al, U.S. Pat. No. 5,503,828 ("the ISI method"). The viability of ammonium chloride back-flushed leukocytes is more than 95% leukocytes isolated by the method of the invention.

Advantageously, the described back-flushing process can easily be scaled up to handle a large number of filters with any automated system. Unlike the Histopaque™ method for retrieving filter-bound leukocytes, the ammonium chloride ($NH_4Cl$) flushing method is not limited to research-scale. Back-flushing with ammonium chloride ($NH_4Cl$) can be automated and scaled up to large production in an industrial setting. For example, this can be achieved using manifold set up, where multiple filters are attached to multiple tubes and connected to a single pump.

Back-flushed leukocytes can then be used for cytokine production, i.e., interferon production after Sendai virus stimulation, for isolation of specific blood cells for immune function study or for immunotherapy. When interferon is produced from the retrieved leukocytes, an interferon titer of $2.3-3.5 \times 10^4$ units per mL, as determined by immunoradiometric assay (RMA) assay-can be obtained by these retrieved leukocytes. This interferon titer is comparable to the titer obtained from leukocytes isolated from buffy coats after ammonium chloride treatment. For comparison, see for example U.S. Pat. No. 5,503,828. Interferon productivity from filters processed 24 to 48 hours after blood drawing was similar and comparable to leukocytes purified from buffy coats processed within 24 hours. This is surprising in view of published reports that filters must be processed within 24 hours in order to recover the leukocytes, [Longley et al, supra, at page 37]. The ammonium chloride was able to both lyse the red blood cells (hemolysis) and dissolve the clumps in the filter formed during storage over time. Other equivalent hemolysis solutions are known to those in the art and may be substituted for the ammonium chloride used in the back-flushing of leukocytes from used filters.

In order that this invention may be better understood the following example is set forth. This example is for the purpose of illustration only and not to be construed as limiting the scope of the invention.

EXAMPLE

In this example we describe a process for the recovery of functional human leukocytes from Pall RCM® filters which are normally used by blood centers to prepare a leukocyte depleted blood product and commonly discarded after use.

Commercially available from Pall Corporation, used Pall RCM filters were obtained from American Red Cross, Baltimore after leukodepletion of red blood cells preparations. Each filter represents one unit of blood. Filters were back-flushed with various media including phosphate buffered saline ("PBS"), PBS containing glycerol and trypsin, etc., L-glutamin supplemented minimum essential medium containing Eagle's salts and tricine ("LMEM") and ammonium chloride. The media was back-flushed with the use of a peristaltic pump. The speed of the peristaltic pump used to back-flush filters was varied from 20 to 90 rpm. The wash was then centrifuged at one thousand RPM for seven minutes and cells were resuspended in LMEM for induction.

Our results indicated that the maximum number of cells were recovered when cold (4° C.) 0.83% ammonium chloride was used. In addition, we obtained a maximum recovery of cells using the following optimized conditions:

(a) a minimum of five hundred ml of ammonium chloride per filter to recover the highest number of cells;

(b) a speed of 60 rpm with the specified size of tubing at a flow rate of 172 ml per minute (see Table 1 for results).

TABLE 1

Interferon Production from Leukocytes Recovered from Pall RCM Filters
Leukocyte recovery and speed of the peristaltic pump

| Speed (rpm) | Recovery (cells/filter) | Percent Viability | Interferon Production (IRMA U/ml)* | Percent of Control** |
|---|---|---|---|---|
| 20 | $5.5 \times 10^8$ | 99 | 29092 | 83 |
| 30 | $6.3 \times 10^8$ | 98 | 24452 | 69 |
| 40 | $6.5 \times 10^8$ | 98 | 22530 | 64 |
| 50 | $7.1 \times 10^8$ | 98 | 35024 | 100 |
| 60 | $7.8 \times 10^8$ | 98 | 23694 | 67 |
| 70 | $3.5 \times 10^8$ | 99 | 17000 | 48 |
| 80 | $3.4 \times 10^8$ | 97 | 33000 | 94 |
| 90 | $3.3 \times 10^8$ | 97 | 16892 | 48 |

*$5 \times 10^6$ PBL/ml were used during induction
**Interferon production from leukocytes isolated from buffy coats (U.S. Pat. No. 5,503,828)

We processed the filters after a storage period of either 24 hours or 48 hours at 4° C. The results from these experiments are shown in Table 2. We observed some variations from filter to filter. Overall, however, the results at 24 hours and at 48 hours were comparable, indicating that the ammonium chloride was able to dissolve any clumps of cells formed after 24 or 48 hours of collection, as well as lyse the red blood cells. Storage of filters for more than 48 hours, i.e., 72 hours or longer, would also be feasible for isolation of leukocytes and the use of these leukocytes for production of interferons.

TABLE 2

Interferon Production from Leukocytes Recovered
from Pall RCM Filters
Time After Blood Drawing

| Experiments | Recovery (PBL/filter) | Percent Viability | Interferon Production (IRMA U/ml) | Percent of Control |
|---|---|---|---|---|
| 1 | $5 \times 10^8$ | 87 | 33165 | 94 |
| 2 | $3.5 \times 10^8$ | 98 | 20916 | 59 |
| 3 | $7.0 \times 10^8$ | 96 | 22897 | 65 |
| 4 | $5.1 \times 10^8$ | 99 | 24082 | 68 |
| 5 | $4.6 \times 10^8$ | 95 | 28048 | 80 |
| 6 | $5.6 \times 10^8$ | 97 | 37370 | 106 |

Exp. 1, 2 and 3 processed after 24 hr after blood drawing.
Exp. 4, 5 and 6 processed after 48 hrs after blood drawing.

Using our optimized parameters we recovered leukocytes in a range between 6 and $8 \times 10^8$ cells per filter with a viability of greater than 95%. We observed that the composition of cell types is similar to that which can be obtained from buffy coats using differential staining.

Recovered leukocytes were capable of producing interferon when induced with Sendai virus. Interferon yields in the initial experiments were between 65 and 85 percent of that obtained by leukocytes from buffy coats. Our yield was improved to almost 100% when we optimized our procedures. The total time required to process each filter was approximately one hour. The results from our studies indicate that blood filters are a convenient and ready source of human PBL for the production of interferons.

In our experiments, regarding induction of interferon with the retrieved leukocytes, we observed clumping of cells at the time of virus addition which resulted in inconsistent interferon titers. In order to reduce cell clumping during virus addition, the timing of ammonium chloride treatment was optimized. We observed that an initial incubation of filters for 10–20 minutes on ice after first recovery and an additional wash with ammonium chloride and an incubation of recovered leukocyte solution for 10–15 minutes on ice was optimal for interferon production. Using these criteria, we obtained a similar or higher yield of interferon as produced from buffy coat-isolated leukocytes (see Table 3).

TABLE 3

Recovery of Leukocytes from Leukotrap ® Filters and
Interferon Induction
Optimal Recovery Yield and Interferon Production

| Filter No. | Number of Cells/Filter | Interferon Production (IRMA U/ml) | Percent of Control |
|---|---|---|---|
| 1 | $9.2 \times 10^8$ | 47696 | 136 |
| 2 | $7.8 \times 10^8$ | 48932 | 139 |
| 3 | $7.8 \times 10^8$ | 42688 | 121 |
| 4 | $7.4 \times 10^8$ | 43148 | 123 |

Note:
Each filter flushed with 500 ml of Ammonium chloride and incubated for 20 min on ice followed by another wash for 10 min. Filters processed at 24 hrs and $5 \times 10^6$ PBL/ml used during induction.

In summary, using the above-described method, we recovered about 50% of PBL from each filter ($6-8 \times 10^8$) as compared to typical recovery from buffy coats ($1.4 \times 10^9$) using published methods [See, for example, Cantell, "Production of Human Leukocyte Interferon", Methods in Enzymology, 78:29–38 (1981) and Testa et al, U.S. Pat. No. 5,503,828]. These recovered leukocytes produced similar interferon titers as compared with buffy coat leukocytes under optimized conditions. Advantageously, filters were found to be capable of storage for a period of 48 hours after blood drawing without exhibiting a significant loss in interferon yields. In contrast, buffy coat-isolated leukocytes lose 50% of their interferon inducibility after storage of 48 hours.

While we have presented a number of embodiments of this invention our basic construction can be altered to provide other embodiments which use the processes of this invention. Therefore, it will be appreciated that the scope of this invention is to be defined by the claims attached hereto rather than by the specific embodiments which have been presented by way of example.

We claim:

1. A method of recovering functional human leukocytes from blood filters used to deplete leukocyte content from any leukocyte-containing blood cell suspension, comprising the steps of:

(a) obtaining filters containing leukocytes which have been depleted from leukocyte-containing blood cell suspensions;

(b) back-flushing the filters with a hemolysis solution comprising cold ammonium chloride or an equivalent solution;

(c) incubating the back-flushed filters on ice;

(d) back-flushing the incubated filters with the hemolysis solution;

(e) centrifuging the hemolysis solution-containing blood cell suspension; and (f) isolating pure leukocytes.

2. The method according to claim 1 wherein the hemolysis solution comprises between 0.7% (w/v) and 0.9% (w/v) ammonium chloride at a temperature of between 2° C. and 8° C.

3. The method according to claim 2, wherein the ammonium chloride is at a temperature of 4° C. and is 0.83% (w/v).

4. The method according to claim 2, wherein 500 ml of ammonium chloride is used per filter.

5. The method according to claim 1, additionally including the use of a peristaltic pump at a speed of between 20 and 90 rpm.

6. The method according to claim 5, wherein the speed is 60 rpm.

7. The method according to claim 1, wherein the filters are incubated for 10 to 20 minutes at a temperature of 4° C.

8. The method according to claim 1, wherein the leukocytes are recovered from the used filter within 72 hours after the leukocyte-containing blood cell suspension is passed through the filter.

9. The method according to claim 8, wherein the blood cell suspension is passed through the filter 24 hours before recovery of leukocytes.

10. The method according to claim 8, wherein the blood cell suspension is passed through the filter 48 hours before recovery of leukocytes.

11. The method according to claim 1, wherein the filters obtained in (a) have been used for red blood cell preparation.

12. The method according to claim 1, wherein the filters obtained in (a) have been used for platelet preparation.

13. A method of recovering purified leukocytes from a filter containing leukocytes which have been depleted from leukocyte-containing blood cell suspensions, said method comprising the steps of (a) back-flushing the filter containing leukocytes with a hemolysis solution comprising ammonium chloride at a temperature of between 2 to 8° C.;

(b) incubating the back-flushed filter at a temperature of about 4° C.;

(c) back-flushing the incubated filter with the hemolysis solution;

(d) centrifuging the hemolysis solution-containing blood cell suspension; and (e) recovering purified leukocytes.

14. The method according to claim 13, wherein the hemolysis solution comprises 500 ml ammonium chloride per filter.

15. The method according to claim 14, wherein the hemolysis solution comprises 0.83% ammonium chloride.

16. The method according to claim 13, wherein the back-flush uses a peristaltic pump at a speed of 60 rpm and a flow rate of about 170 ml per minute.

* * * * *